United States Patent [19]

Booth

[11] Patent Number: 5,037,414
[45] Date of Patent: Aug. 6, 1991

[54] SELF-CONTAINED DISPOSABLE DIAPER
[75] Inventor: John W. Booth, Irving, Tex.
[73] Assignee: Edward R. Gutierrez, Grand Prairie, Tex.
[21] Appl. No.: 475,787
[22] Filed: Feb. 6, 1990
[51] Int. Cl.[5] ............................................. A61F 13/00
[52] U.S. Cl. .................................................. 604/385.1
[58] Field of Search .......................... 604/385.1, 389.1
[56] References Cited

U.S. PATENT DOCUMENTS

| | | | |
|---|---|---|---|
| 3,369,545 | 2/1968 | Wanberg | 604/366 |
| 3,865,110 | 2/1975 | Trarerse | 604/372 |
| 3,920,019 | 11/1975 | Schaar | 604/385.1 |
| 4,430,087 | 2/1984 | Azpiri | 604/385.1 |
| 4,604,096 | 8/1986 | Dean et al. | 604/389.2 |

Primary Examiner—Stephen C. Pellegrino
Assistant Examiner—Gary Jackson
Attorney, Agent, or Firm—Dennis T. Griggs

[57] ABSTRACT

A disposable diaper has an absorbent pad confined between a permeable front panel and a liquid impervious back panel, with a flexible containment pouch being enclosed within a pocket adjacent to the back panel. A perforated closure panel secures the containment pouch within the pocket. The containment pouch is carried within the closure panel pocket while the diaper is being worn. For disposal of the diaper, the closure panel is ruptured and the containment pouch is removed from the pocket. The diaper is then rolled up and inserted into the containment pouch for disposal.

4 Claims, 4 Drawing Sheets

SELF-CONTAINED DISPOSABLE DIAPER

FIELD OF THE INVENTION

This invention relates generally to disposable diapers, and in particular to disposable diapers adapted for sanitary disposal.

BACKGROUND OF THE INVENTION

A variety of disposable diapers are in widespread use. Disposable diapers are available in sizes ranging from newborn to adult with each size being adapted to meet the size requirements of the individual. Disposable diapers have various absorbency characteristics adapted to accommodate the differences of daytime usage versus nighttime usage. There have been improvements in the materials and designs of the absorbent pad to minimize dampness, discomfort and rashing while maximizing absorbency. Elastic waist and leg bands enhance the diaper's fit and comfort while minimizing leakage and odor. For fastening, reusable adhesive fasteners are used in lieu of safety pins to provide additional safety and convenience. Disposable diapers can be bought in a variety of decorative designs and colors.

After being soiled, disposable diapers are usually folded and secured by the reusable adhesive fasteners. This containment design does not stop the leakage of odor or bacteria. Additionally, it can create a nuisance when discarding, resulting in unsanitary environments. Typically, disposal is made by discarding the diaper into a garbage can to capture leakage and odor. The garbage can usually includes a cover that requires the application of antiseptic and deodorizing sprays. When traveling, one must either find a sealed container or carry a portable sealed container.

The foregoing improvements have attempted to meet customer requirements. However, the soiled diaper disposal problem has not been completely overcome.

DESCRIPTION OF THE PRIOR ART

Various attempts have been made to design a disposable diaper with a disposable containment system. U.S. Pat. No. 3,927,674 which issued to Charles H. Schaar uses a bag that is attached to the diaper. The bag is a separate compartment which is folded for storage. U.S. Pat. No. 3,620,217 which issued to Dale A. Gellert employs reusable fasteners for sealing the diaper. U.S. Pat. No. 4,182,236 which issued to Charles A. Black discloses a thin, folded bag attached to sanitary napkins. U.S. Pat. No. 3,920,019 which issued to Charles A. Schaar uses a folded sheet attached to the diaper as a disposal cover. U S. Pat. No. 3,877,432 which issued to Dale A. Gellert uses a two-ply back sheet to make a disposable bag or sheath. The absorbent pad is partially removed from the two-ply back sheet prior to inverting the bag. U.S. Pat. No. 3,865,110 describes a containment bag where the absorbent pad is disengaged from the back sheeting prior to inverting the bag. U.S. Pat. No. 3,369,545 which issued to Joseph S. Wanberg describes a pouch attached to the back surface of the absorbent pad.

SUMMARY OF THE INVENTION

An object of the present invention is to provide an improved disposable diaper having a containment pouch to prevent leakage and odor from a soiled diaper.

According to a preferred embodiment of the present invention, a disposable diaper includes an absorbent pad assembly having a pair of waistline portions, a permeable front panel and a substantially liquid impervious back panel; a flexible containment pouch enclosed within a pocket adjacent to the back panel of said pad assembly, and having a perforated closure panel securing the containment pouch within the pocket. The containment pouch is carried within the closure panel pocket while the diaper is being worn. For disposal of the diaper, the closure panel is ruptured and the containment pouch is removed from the pocket. The diaper is then rolled up and inserted into the containment pouch. The pouch is thereafter sealed and discarded into an appropriate trash receptacle.

Further objects, features and advantages will be apparent from the following description of the preferred embodiment of the invention.

BRIEF DESCRIPTION OF THE DRAWINGS

So that the manner in which the above-featured advantages and objects of the present invention will be more readily understood, the construction and operation of a preferred embodiment will now be described with reference to the accompanying drawings wherein.

DETAILED DESCRIPTION OF THE PREFERRED EMBODIMENT

Figure 1:
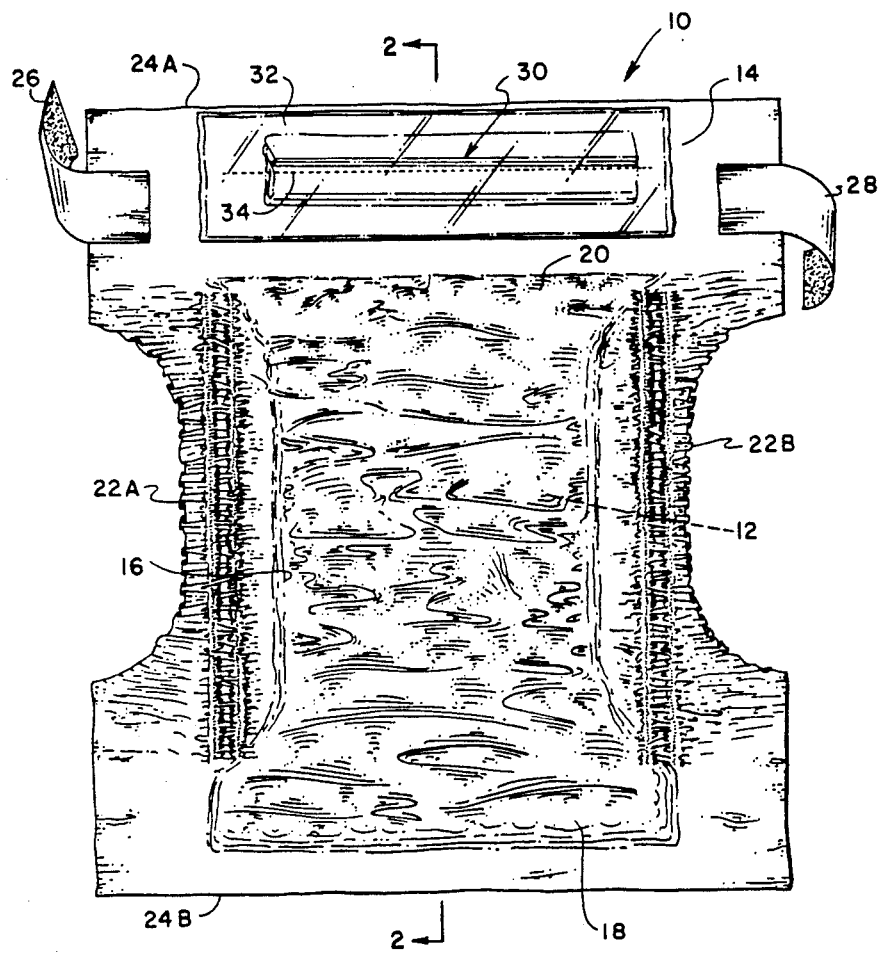
FIG. 1 is a back plan view of a disposable diaper constructed according to the present invention.

In the description which follows, like parts are marked throughout the specification and drawings with the same reference numerals, respectively. The drawings are not necessarily to scale and the proportions of certain parts have been exaggerated or shown in schematic form in the interest of clarity and conciseness.

Figure 2:
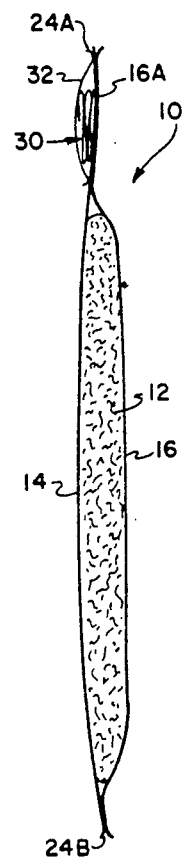
FIG. 2 is a vertical longitudinal sectional view of the diaper shown in FIG. 1.

Referring to FIGS. 1 and 2, there is shown a disposable diaper 10 having an absorbent pad 12. The pad 12 has a flexible, liquid impervious back panel 14. A fluid permeable front panel 16 defines a substantial portion of the front surface of the diaper 10, with the pad 12 being confined between the back panel 14 and front panel 16. The diaper 10 has a waistline portion 18, a back portion 20 and a pair of side edges 22A, 22B and end edges 24A, 24B. The diaper 10 includes a pair of adhesive strips 26, 28 attached to one end edge 24A of the diaper 10 for securing the diaper to the individual. The specific construction of the diaper pad 12 can include any of the absorbent diaper pad materials which are presently available, and various size and absorbency specifications may be utilized to good advantage in connection with the present invention.

Figure 3:
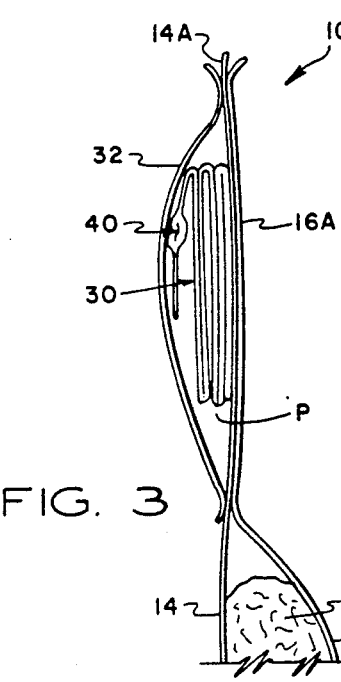
FIG. 3 is an enlarged sectional view of the disposable diaper of FIG. 2 showing a containment pouch sealed within a pocket.

The front and rear panels 14, 16 are sealed together along marginal edge portions 14A, 16A as shown in FIG. 3. According to an important feature of the present invention, a containment pouch 30 is enclosed within a pocket P along the back marginal edge 24A of the diaper. In this arrangement, the pocket P is sealed by a frangible panel 32 which is heat sealed along its edges onto the marginal side surface of the back panel 14. Preferably, the frangible panel 32 is scored by a longitudinally extending perforation line 34 to facilitate opening access to the containment pouch 30.

Figure 4:
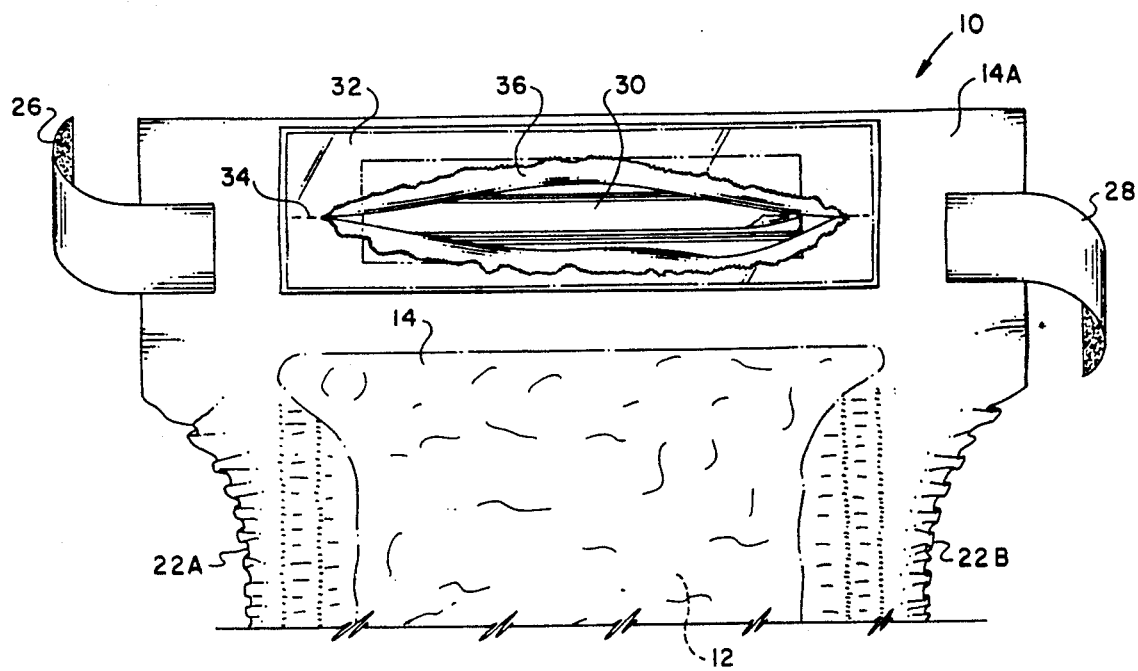
FIG. 4 is a back plan view of the disposable diaper shown in FIG. 1 with the pocket panel ruptured for removal of the containment pouch.
Figure 5:
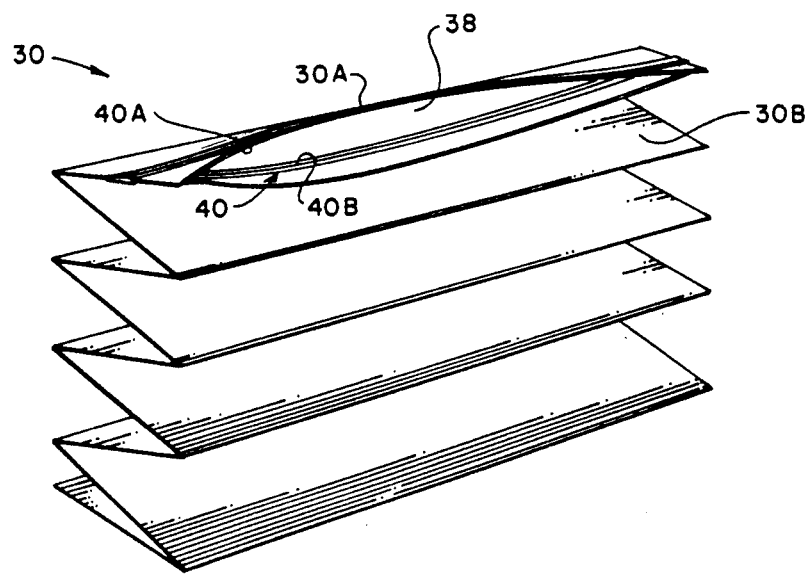
FIG. 5 is a perspective view of the containment pouch shown in FIG. 1 and FIG. 3.

Referring now to FIGS. 4 and 5, the containment pouch 30 is removable from the pocket P through a rupture opening 36 which is produced by tearing the panel 32 along the perforation line 34. The containment pouch 30 is constructed of a flexible plastic material, and is folded in a stack of accordion pleats as indicated by FIG. 3 and FIG. 5. The containment pouch 30 is formed by side panels 30A, 30B which are sealed along marginal edges and along the bottom of the pouch. The top of the containment pouch 30 has an opening 38 which can be sealed by a variety of closure means, for example, a tacky adhesive strip or a zipper. In the embodiment shown in FIG. 5, the opening 38 is sealed by a ZIPLOC ® closure 40 having interlocking male and female sealing elements 40A, 40B. Preferably, the closure means provides an airtight seal.

The containment pouch 30 is preferably oriented with the opening 38 and closure means 40 parallel to the marginal end 24A (FIG. 1). The containment pouch 30 must be of adequate size to enclose a soiled diaper. During assembly, the containment pouch 30 is folded in the manner shown in FIG. 5, and is secured between the enclosure panel 32 and the back panel 14. The enclosure panel 32 is heat sealed along its marginal edges against the back panel 14, thereby securing the containment pouch 30 within the pocket P until it is ready for use.

Figure 6A:
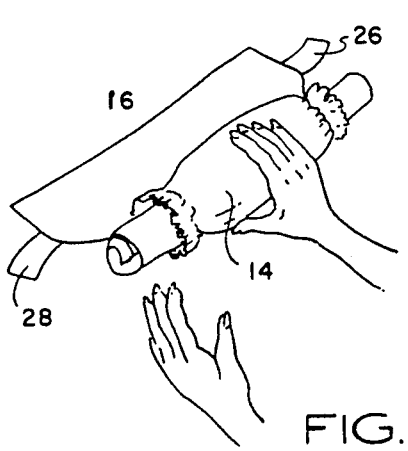
FIGS. 6A through 6E are perspective views illustrating the method of sealing the disposable diaper of the present invention.
Figure 6B:
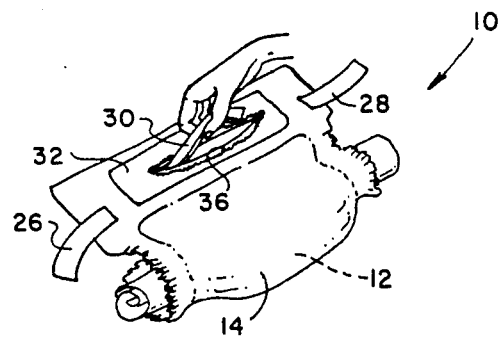
Figure 6C:
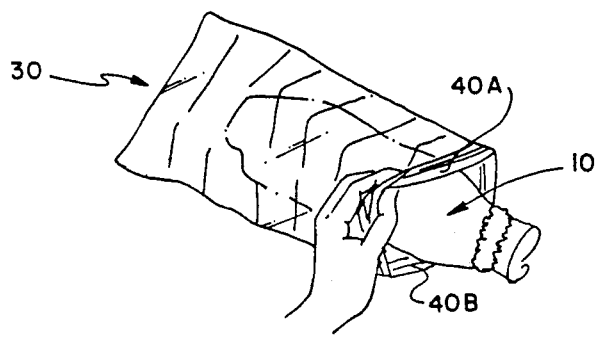
Figure 6D:
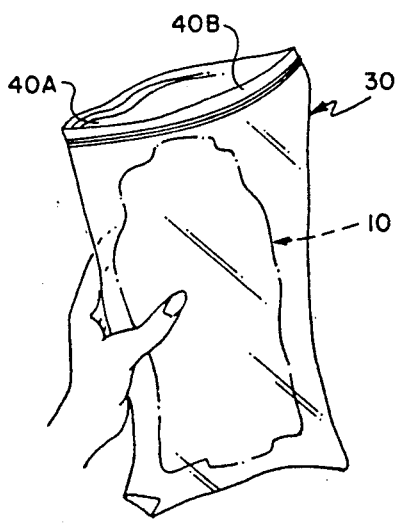
Figure 6E:
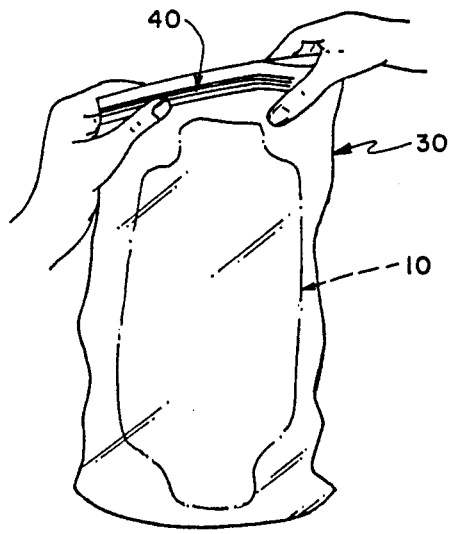

Referring now to FIGS. 6A through 6E, when it is desired to dispose of a soiled diaper 10, the diaper 10 is prepared for insertion into the containment pouch 30 by rolling the diaper with the back panel 14 being engaged against the front panel 16. After the diaper 10 has been rolled up, it is turned over and the closure panel 32 is ruptured along the perforated line 34 to expose the containment pouch 30. After the containment pouch 30 has been removed through the rupture opening 36, the pouch is opened and the rolled up diaper 10 is inserted through the opening 38 as shown in FIG. 6C. After the rolled up diaper 10 is fully inserted into the containment pouch 30, the pouch is secured by pressing the ZIPLOC ® interlocking closure fasteners 40A, 40B together as shown in FIG. 6D and FIG. 6E. After the containment pouch 30 has been sealed, it is ready for sanitary disposal without leakage or odors.

Figure 7:
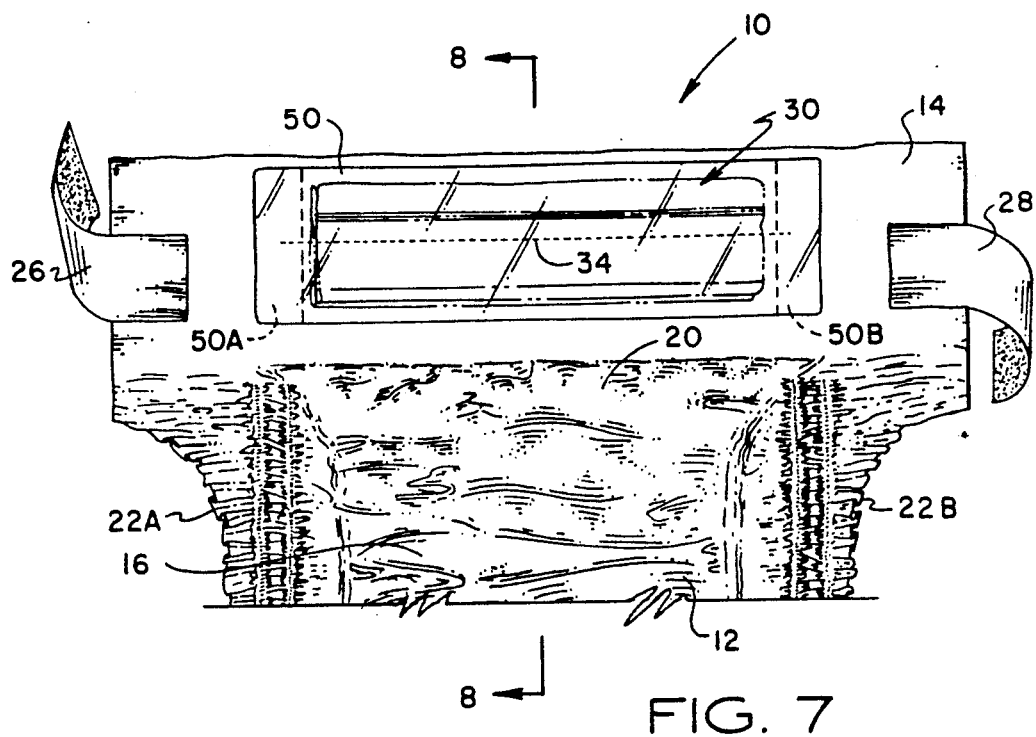
FIG. 7 is a back plan view of a disposable diaper constructed according to an alternative embodiment of the present invention; and, FIG. 8 is an enlarged sectional view taken along the line 8—8 of FIG. 7.
Figure 8:
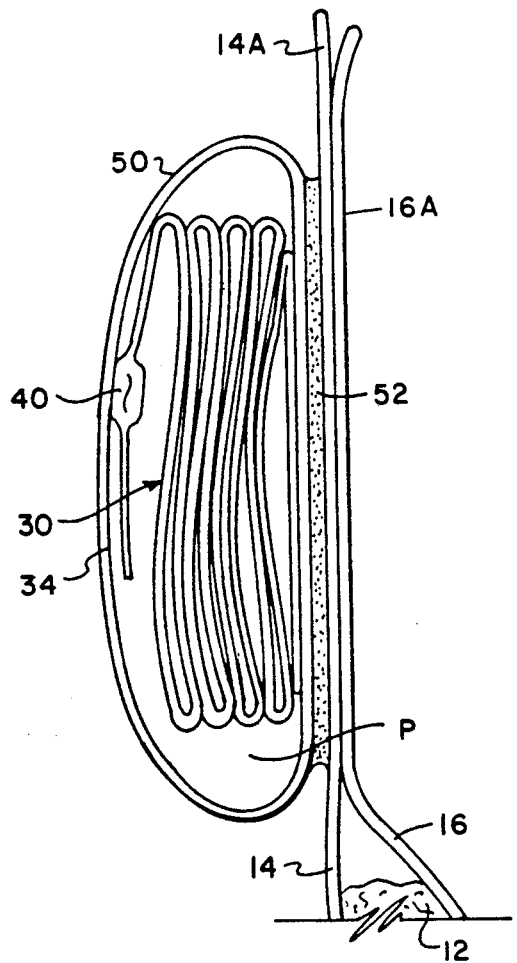

Referring now to FIG. 7 and FIG. 8, an alternative containment pouch arrangement is illustrated. In this alternative embodiment, the pocket P is enclosed and sealed by a tubular sleeve 50. The opposite ends 50A, 50B of the tubular sleeve are folded inwardly and are heat sealed during a separate manufacturing step. After the containment pouch 30 has been sealed, the tubular sleeve 50 is bonded onto the marginal side surface of the back panel 14 by a layer of adhesive 52. The tubular sleeve 50 is constructed of a frangible sheet material. Preferably, the frangible sleeve 50 is scored by a longitudinally extending perforation line 34 to facilitate opening access to the containment pouch 30.

The built-in containment pouch of both embodiments provides clean and convenient disposal. It can be dropped in any appropriate container without worrying about any of the attendant odors and bacterial problems associated with soiled diapers. The use of this invention will provide a more sanitary environment in homes, child care facilities, hospitals, nursing homes and while traveling.

Although the invention has been described with reference to specific embodiments, the foregoing description is not intended to be construed in a limiting sense. Various modifications to the disclosed embodiments as well as alternative applications of the invention will be suggested to persons skilled in the art by the foregoing specification and illustrations. It is therefore contemplated that the appended claims will cover any such modifications, applications or embodiments as fall within the true scope of the invention.

What is claimed is:

1. A disposable diaper comprising, in combination:
an absorbent pad assembly having a liquid permeable front panel, a substantially liquid impervious back panel and an absorbent pad secured between said front panel and said back panel;
a sleeve of frangible material secured onto said back panel, said sleeve having a tubular sidewall and first and second closed end portions defining a sealed containment pocket; and
a containment pouch disposed within said containment pocket, said containment pocket having closure means for securing a soiled diaper within said pouch.

2. A disposable diaper as defined in claim 1, said sleeve on its tubular sidewall.

3. A disposable diaper as defined in claim 3, wherein said tubular sleeve is secured onto the liquid impervious back panel by a layer of adhesive.

4. A method for handling a disposable diaper of the type having a liquid permeable front panel, a substantially liquid impervious back panel and an absorbent pad secured between the front panel and the back panel comprising the steps:
enclosing a containment pouch within a tubular sleeve of frangible material;
attaching the tubular sleeve onto the external surface of said back panel;
rolling the disposable diaper with the back panel being rolled against the front panel;
rupturing the tubular sleeve and removing the containment pouch from said containment pocket;
inserting the rolled diaper into the containment pouch; and
sealing the diaper within said containment pouch.

* * * * *